US006774144B1

(12) United States Patent
Dykstra et al.

(10) Patent No.: US 6,774,144 B1
(45) Date of Patent: Aug. 10, 2004

(54) METHODS AND FORMULATIONS FOR THE TREATMENT OF INFECTIOUS BURSAL DISEASE IN AVIAN SUBJECTS

(75) Inventors: Christine C. Dykstra, Auburn, AL (US); James C. Hudson, Carpenteria, CA (US); Sandra Ewald, Auburn, AL (US); Richard R. Tidwell, Pittsboro, NC (US); David W. Boykin, Atlanta, GA (US)

(73) Assignees: The University of North Carolina at Chapel Hill, Chapel Hill, NC (US); Georgia State University Research Foundation, Inc., Atlanta, GA (US); Auburn University, Auburn, AL (US)

( * ) Notice: Subject to any disclaimer, the term of this patent is extended or adjusted under 35 U.S.C. 154(b) by 188 days.

(21) Appl. No.: 09/703,804

(22) Filed: Nov. 1, 2000

Related U.S. Application Data

(60) Provisional application No. 60/162,877, filed on Nov. 1, 1999.

(51) Int. Cl.[7] .............................................. A61K 31/34

(52) U.S. Cl. ........................ 514/461; 514/472; 514/473

(58) Field of Search ................................ 514/461, 472, 514/473

(56) References Cited

U.S. PATENT DOCUMENTS

| | | | | |
|---|---|---|---|---|
| 4,324,794 A | 4/1982 | Tidwell et al. | .............. | 424/273 |
| 5,308,838 A | 5/1994 | McAnalley et al. | | |
| 5,521,189 A | 5/1996 | Boykin et al. | | |
| 5,622,955 A | 4/1997 | Boykin et al. | .............. | 514/256 |
| 5,668,166 A | 9/1997 | Tidwell et al. | | |
| 5,668,167 A | 9/1997 | Tidwell et al. | .............. | 514/411 |
| 6,127,554 A | * 10/2000 | Boykin et al. | .............. | 549/504 |

FOREIGN PATENT DOCUMENTS

| | | |
|---|---|---|
| EP | 0 941 991 A1 | 9/1999 |
| WO | WO 95/19772 | 7/1995 |
| WO | WO 96/40117 | 12/1996 |

OTHER PUBLICATIONS

Luckert, P.D. et al., *Avian Dis.* 18, 243–251 (1974).

Baxendale, W. et al., *Dev. Biol. Stand.* 51, 211–219 (1981).

Lucio, B. et al., *Avian Dis.* 23, 466–478 (1979).

Boykin, D.W. et al., *Eur. J. Med. Chem.* 32, 965–972 (1997).

Tidwell, R. R. et al., *J. Med. Chem.* 21, 613–623 (1978).

Mossman, T. *J. Immunol. Methods* 65, 55–63(1983).

Tidwell, Richard R., et al., *Suppression of Respiratory Syncytial Virus Infectionin Cotton Rats by Bis(5–Amidino–2–Benzimidazolyl)Methane, Antimicrobial Agents and Chemotherapy*, vol. 26, No. 4, pp. 591–593 (Oct. 1984).

Dubovi E.J., et al., *Inhibition of Respiratory Syncytial Virus by Bis(5–amidino–2–benzimidazolyl)methane, Virology*, vol. 103, pp. 502–504 (1980).

Definition of "respiratory syncytial virus", *The American Heritage® Dictionary of the English Language*: Fourth Edition, Internet XP002175541 (2000).

Berghot, Moged Ahmed, et al., *Facile Synthesis of Novel Carbazoles Through Heterocyclization Reactions and Their Antimicrobial Activity, Revue Roumaine de Chimie*, vol. 40, No. 4, pp. 377–386 (1995).

Hildebrandt, Ellen, et al., *Identification and Characterization of an Endo/exonuclease Pheumocystis carinii that is Inhibited by Dicationic Diarylfurans with Efficacy Against Pneumocystis Pneumonia, J. Euk. Microbiol.*, vol. 45, No. 1, pp. 112–121 (1998).

Kumar, A., et al., *Anti–Pneumocystis carinii pneumonia activity of dicationic 2,4–diarylprimidines, Eur. J. Med. Chem.*, vol. 31, pp. 767–773 (1996).

Xiao, Ge, et al., *Inhibition of the HIV–1 Rev–RRE Complex Formation by Unfused Aromatic Cations, Bioorganic & Medicinal Chemistry*, vol. 9, pp. 1097–1113 (2001).

Francesconi, Iris, et al., *2–4 Diphenyl Furan Diamidines as Novel Anti–Pneumocystis carinii Pneumonia Agents, J. Med. Chem.*, vol. 42, pp. 2260–2265 (1999).

International Search Report, International Application No. PCT/US00/30066 dated Jan. 14, 2002.

D. Boykin et al., *Anti–Pneumocystis carinii pneumonia activity of diactionic 2,4–diarylpyrimidines, European Journal of Medicinal Chemistry* 32, No. 12:965–972 (Dec. 1, 1998).

* cited by examiner

*Primary Examiner*—Phyllis Spivack
*Assistant Examiner*—C. Delacroix-Muirheid
(74) *Attorney, Agent, or Firm*—Jenkins, Wilson & Taylor, P.A.

(57) ABSTRACT

In one aspect, the invention relates to a method of treating infectious bursal disease (IBD) in an avian subject in need of such treatment. The method comprises administering to the subject a compound of the formulas (I) through (IV) or a pharmaceutically acceptable salt thereof in an amount sufficient to treat IBD. In another aspect, the invention relates to a method of producing active immunity against infectious bursal virus disease (IBD) in an avian subject. The method comprises administering to a subject an immunogenic-amount of an IBDV vaccine and a compound selected from the compounds of formulas (I) through (IV) described herein. The compound represented by formulas (I) through (IV) is administered in an amount sufficient to induce an immune response in the avian subject.

25 Claims, 5 Drawing Sheets

METHODS AND FORMULATIONS FOR THE TREATMENT OF INFECTIOUS BURSAL DISEASE IN AVIAN SUBJECTS

RELATED APPLICATIONS

This application claims the benefit of U.S. Provisional Application No. 60/162,877, filed Nov. 1, 1999, which is incorporated herein by reference in its entirety.

FIELD OF THE INVENTION

The invention generally relates to methods and formulations for treating infectious bursal disease in avian subjects.

BACKGROUND OF THE INVENTION

Infectious bursal disease virus ("IBDV") causes a highly contagious immunosuppressive disease in avian species (e.g., chickens and turkeys). See Luckert, P. D. et al., *Avian Dis.* 18, 243–251 (1974). The disease is believed to severely deplete the bursa of Fabricius and/or the spleen of the B-cells and other immunoprotective cells necessary for mounting an antibody response to infectious agents. If infectious bursal disease (IBD) does not directly result in death, the resulting immunosuppression can leave the bird susceptible to other infections and reduce its ability to respond to vaccination. Thus, the disease poses a significant problem to the poultry industry.

Vaccination efforts are intended to prevent serious losses from "clinical" IBD in which mortality may exceed five percent and morbidity 100 percent. For example, breeding hens are typically vaccinated with a combination of live virus (e.g., at four to six weeks of age) and inactivated virus (e.g., at 18 to 20 weeks of age). The hens are typically monitored serologically for IBDV antibody to ensure protection for themselves, and to maintain adequate maternal IBDV antibody levels in the chicks. Maternal antibody may provide protection for several days (e.g., three to seven days) or, if oil emulsion type vaccines are employed, four to five weeks. The level of protection has been reported to vary from chick to chick. See Baxendale, W. et al., *Dev. Biol. Stand.* 51, 211–219 (1981) and Lucio, B. et al., *Avian Dis.* 23, 466–478 (1979). Some commercial operations also vaccinate day old chicks in ovo, and later with additional field boosts (typically one or more). The timing of the vaccination is believed to be important. The proper time to vaccinate typically varies depending upon maternal antibody level, route of vaccination, and virulence of the vaccine virus.

In recent years, "subclinical" IBDV infection, associated with variant vaccine strains, have become more common. The disease typically appears less severe and the inflammatory response in the bursa usually is less pronounced than with full-blown IBDV infection. Nonetheless, immunosuppression may still occur. Infection and immunosuppression continue to be common despite the substantial investment by poultry producers in the vaccines, serological monitoring, and labor involved in vaccination administration. Accordingly, there is a need in the art for more effective methods of treating and preventing IBD than are currently practiced.

SUMMARY OF THE INVENTION

In one aspect, the invention relates to a method of treating infectious bursal disease (IBD) in an avian subject in need of such treatment. The method comprises administering to the subject a compound selected from the group consisting of formulas (I) through (IV):

(I)

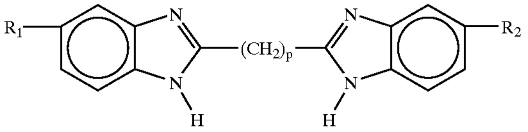

(II)

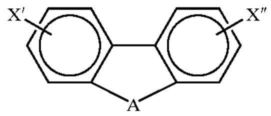

(III)

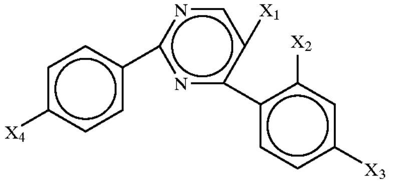

and (IV)

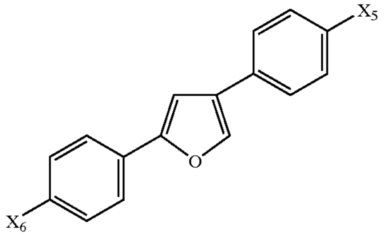

and the pharmaceutically acceptable salts thereof, wherein:

p is an integer ranging from one to eight;

A is selected from O, S, and NR, wherein R may be H or loweralkyl;

X', X", $X_3$, $X_4$, $X_5$, $X_6$, $R_1$, $R_2$, $R_3$, and $R_4$ are independently selected and each represented by loweralkyl, loweralkoxy, alkoxyalkyl, hydroxyalkyl, aminoalkyl, alkylaminoalkyl, cycloalkyl, aryl, alkylaryl, halogen or:

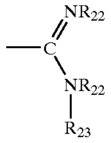

wherein:

each $R_{22}$ and $R_{23}$ is independently selected from the group consisting of H, loweralkyl, alkoxyalkyl, hydroxyalkyl, aminoalkyl, alkylaminoalkyl, cycloalkyl, aryl, and alkylaryl, or two $R_{22}$ groups together represent $C_2$–$C_{10}$ alkyl, hydroxyalkyl, or alkylene, or the two $R_{22}$ groups together represent cycloalkyl, or:

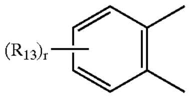

wherein r is from one to three and $R_{13}$ is H,

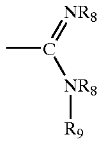

or —$CONHR_{10}NR_{11}R_{12}$, wherein:

$R_{10}$ is loweralkyl; $R_{11}$ and $R_{12}$ are independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, and alkylaryl, or two $R_8$ groups together represent $C_2$–$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl; wherein X' and X" may be in the meta or para positions;

$X_1$ and $X_2$ are independently selected from the group consisting of H, loweralkyl, and loweralkoxy;

and wherein the compound represented by formulas (I), (II), (III), or (IV) is administered in an amount to treat the IBDV.

In one embodiment, the compound is represented by the formula:

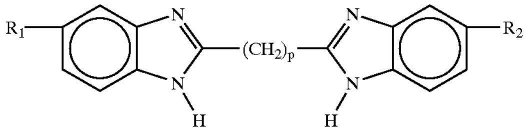

wherein p, $R_1$, and $R_2$ are as previously defined. In this embodiment, the compound is preferably represented by the formula:

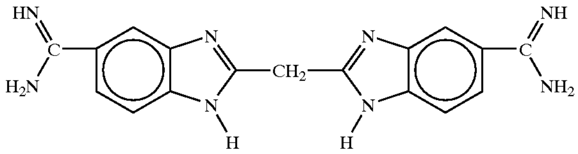

In another embodiment, the compound is represented by the formula:

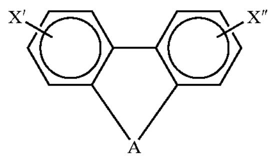

wherein X', X", and A are as previously defined. In this embodiment, the compound is preferably represented by the formula:

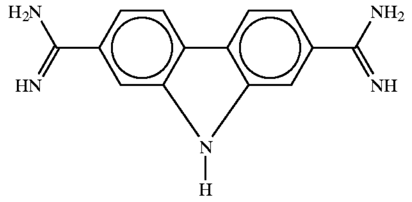

In another embodiment, the compound is represented by the formula:

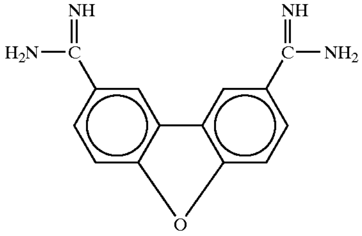

In yet another embodiment, the compound is represented by the formula:

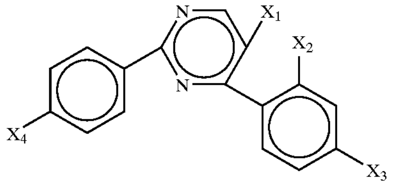

wherein $X_1$, $X_2$, $X_3$, and $X_4$ are as previously defined. In this embodiment, the compound may be of the formula:

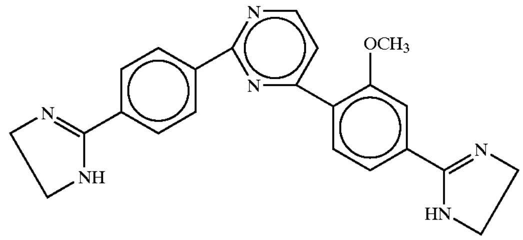

The compound in this embodiment may also be of the formula:

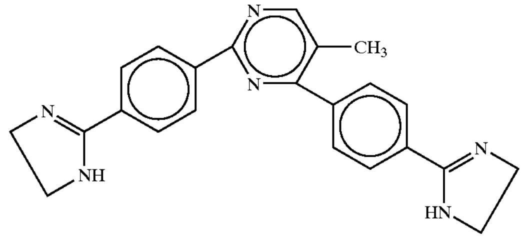

In still another embodiment, the compound is represented by the formula:

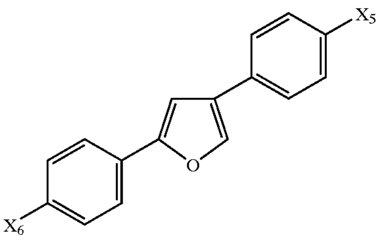

wherein $X_5$ and $X_6$ are as defined above. A preferred compound in this embodiment is represented by the formula:

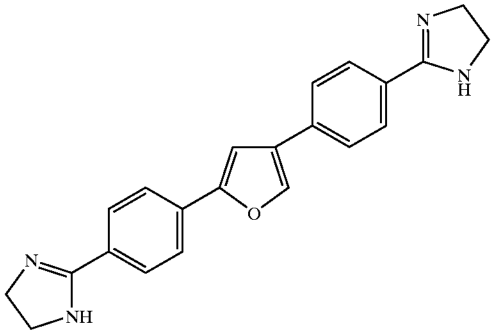

In another aspect, the invention provides a method for producing active immunity against infectious bursal virus disease (IBDV) in an avian subject. The method comprises administering to a subject an immunogenic-amount of an IBDV vaccine and a compound selected from the group consisting of formulas (I) through (IV) or a pharmaceutically acceptable salt thereof.

Another aspect of the invention relates to a pharmaceutical formulation for the treatment of IBD, comprising a compound of the present invention as set forth above in a pharmaceutically acceptable carrier.

BRIEF DESCRIPTION OF THE DRAWINGS

FIG. 1 illustrates the effect of drug concentration on IBDV replication.

DETAILED DESCRIPTION OF THE PREFERRED EMBODIMENTS

Figure 1:
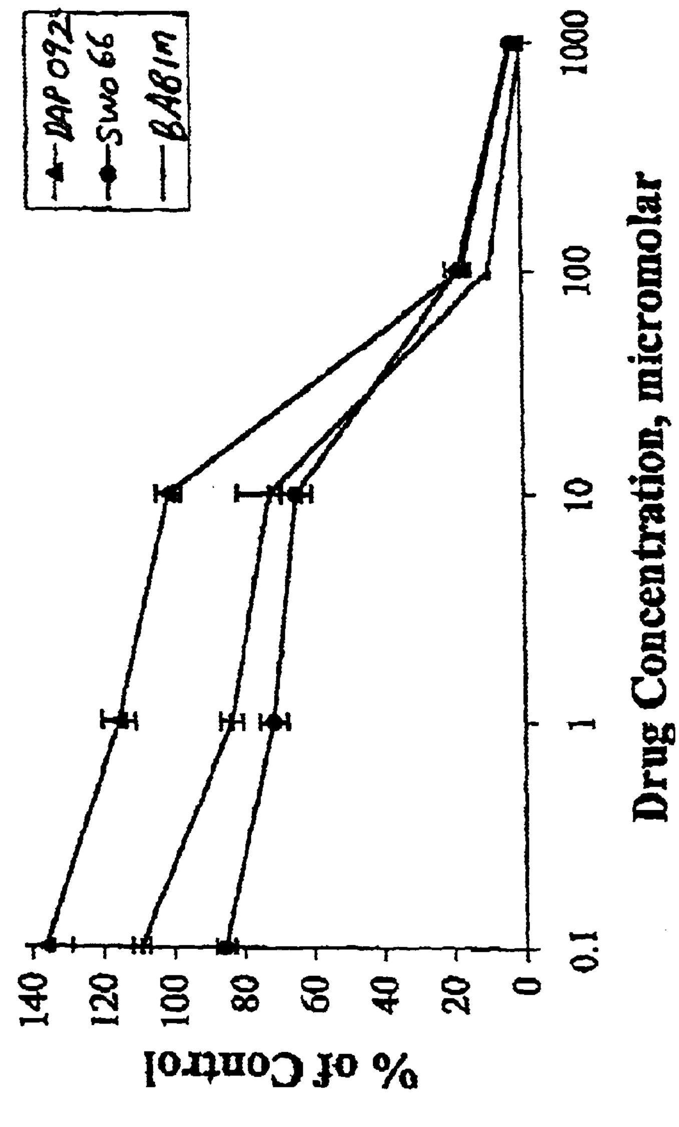
FIG. 1 is a graphical illustration of single step growth curves of IBDV in chick embryo fibroblasts treated with the drugs SW066, DAP092, and BABIM.

The present invention now will be described more fully hereinafter with reference to the accompanying specification and drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

With respect to the compounds of the formulas (I) through (IV), as used herein, the term "alkyl" refers to C1–10 inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. The term "lower alkyl" refers to C1 to C4 linear or branched alkyl, such as methyl, ethyl, propyl, butyl, isopropyl, sec-butyl, and tert-butyl. The term "halogen" has its conventional meaning and refers to fluorine, chlorine, bromine, and iodine. The term "cycloalkyl" as used herein refers to C3 to C6 cyclic alkyl, such as cyclopropyl, cyclobutyl, cyclopentyl, and cyclohexyl. The term "aryl" as used herein refers to C3 to C10 cyclic aromatic groups such as phenyl, naphthyl, and the like, and includes substituted aryl groups such as, but not limited to, tolyl. Heterocyclic aromatic rings are also included in this definition of "aryl." Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like. The term "hydroxyalkyl" as used herein refers to C1 to C4 linear or branched hydroxy-substituted alkyl, i.e., $—CH_2OH$, $—(CH_2)_2OH$, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., $—NH_2$, $—NHCH_3$, $—N(CH_3)_2$, etc. The term "oxyalkyl" as used herein refers to C1 to C4 oxygen-substituted alkyl, i.e., $—OCH_3$, and the term "oxyaryl" as used herein refers to C3 to C10 oxygen-substituted cyclic aromatic groups. The term "loweralkoxy" or "alkoxyalkyl" as used herein refers to C1 to C4 linear or branched alkoxy, such as methoxy, ethoxy, propyloxy, butyloxy, isopropyloxy, and t-butyloxy.

The compounds of the present invention are also useful in the form of their pharmaceutically acceptable salt forms. Such salts may include, but are not limited to, the gluconate, lactate, acetate, tartarate, citrate, phosphate, borate, nitrate, sulfate, and hydrochloric salts of the compounds.

The compounds represented by the formulas (I) through (IV) used in the methods of the invention may be formed by synthesis procedures that are known in the art and also described in the examples below. Examples of methods for forming these compounds are illustrated in U.S. Pat. Nos. 4,324,794 and 5,668,167 to Tidwell et al. and U.S. Pat. No. 5,622,955 to Boykin et al., the disclosures of which are all incorporated herein by reference in their entirety. For example, in the compound of formula (II) when A is nitrogen, the compound may be formed by first preparing an appropriate intermediate, such as 2,4-bis(4-bromophenyl) pyrimidine. The intermediate may be prepared by the base-promoted condensation of 4-bromobenzamidine and 1-dimethylamino-3-dimethylimmonio-1-(4-bromophenyl)-1-propene, according to known methods. The bis-nitrile is obtained by reacting copper(I) cyanide with the above-described intermediate in refluxing dimethylformamide (DMF), according to known techniques. The bis-nitrile may then be converted to the imidate ester, and subsequently the compound of formula (II), utilizing known techniques. As another example of the synthesis of compounds of the present invention, the compound of formula (III) may be made in accordance with the methods outlined in D. W. Boykin, et al., *Eur. J. Med. Chem.* 32, 965–972 (1997), the disclosure of which is incorporated herein by reference in its entirety.

As noted above, the methods of the present invention are useful for treating infectious bursal disease (IBD). The term "infectious bursal disease virus" (IBDV), as used herein, encompasses all IBDV strains and all serotypes and variants thereof, including live, attenuated, killed or otherwise inactivated forms. Exemplary strains include, but are not limited to, the D78, PBG98, STC, CGLS, DS326, VR2161, RS593, Luckert, Delaware Variant A and the Delaware Variant E strains of the bursal disease virus, as well as the bursal disease virulent challenge virus.

In one embodiment of the invention, an avian subject is administered a therapeutically-effective amount of the compound of formulas (I) through (IV), or pharmaceutically acceptable salt thereof. A "therapeutically-effective" amount as used herein is an amount of a compound of formulas (I) through (IV) that is sufficient to alleviate (e.g., mitigate, decrease, reduce) at least one of the symptoms associated with IBD. It is not necessary that the administration of the compound eliminate the symptoms of IBD, as long as the benefits of administration of compound outweigh the detriments. Likewise, the terms "treat" and "treating" in reference to IBD, as used herein, are not intended to mean that the avian subject is necessarily cured of IBD or that all clinical signs thereof are eliminated, only that some alleviation or improvement in the condition of the avian subject is effected by administration of the compound of formulas (I) through (IV).

The term "avian" and "avian subjects," as used herein, is intended to include males and females of any avian species, but is primarily intended to encompass poultry which are commercially raised for eggs, meat or as pets. Accordingly, the terms "avian" and "avian subject" are particularly intended to encompass chickens, turkeys, ducks, geese, quail, pheasant, parakeets, parrots, and the like. Chickens are the preferred avian subjects. The avian subject may be a hatched bird, which term encompasses newly-hatched (i.e., about the first three days after hatch) as well as post-hatched birds such as, for example, adolescent, and adult birds. The avian subject may also be pre-hatch, i.e., in ovo.

Avian subjects may be administered the compounds described by the present invention by any suitable means. Exemplary means are oral administration (e.g., in the feed or drinking water), intramuscular injection, subcutaneous injection, intravenous injection, intra-abdominal injection, eye drop, or nasal spray. Avian subjects may also be administered the compounds in a spray cabinet, i.e., a cabinet in which the birds are placed and exposed to a vapor containing vaccine, or by coarse spray. When administering the compounds described herein to birds post-hatch, administration by subcutaneous injection or spray cabinet are commonly used techniques.

The compounds of the present invention may also be administered in ovo. The in ovo administration of the compounds involves the administration of the compounds to the avian embryo while contained in the egg. The compounds may be administered to any suitable compartment of the egg (e.g., allantois, yolk sac, amnion, air cell, or into the avian embryo itself), as would be apparent to one skilled in the art. Eggs administered the compounds may be fertile eggs which are preferably in the last half, and more preferably the last quarter, of incubation. Chicken eggs are preferably treated on about day 18 of incubation, although other time periods may be employed. Those skilled in the art will appreciate that the present invention can be carried out at various predetermined times in ovo.

Eggs may be administered the compounds of the invention by any means which transports the compound through the shell. A common method of administration is, however, by injection. For example, the compound may injected into an extraembryonic compartment of the egg (e.g., yolk sac, amnion, allantois, air cell) or into the embryo itself. As an example, the site of injection may be within the region defined by the amnion, including the amniotic fluid and the embryo itself. By the beginning of the fourth quarter of incubation, the amnion is sufficiently enlarged that penetration thereof is assured nearly all of the time when the injection is made from the center of the large end of the egg along the longitudinal axis.

The mechanism of egg injection is not critical, but it is preferred that the method not unduly damage the tissues and organs of the embryo or the extraembryonic membranes surrounding it so that the treatment will not decrease hatch rate. The size of the needle and the length of penetration may be determined by one skilled in the art. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

In another aspect, the invention also relates to a method for producing active, and preferably protective, immunity against IBDV in an avian subject. The method comprises administering to a subject an immunogenic-amount of an IBDV vaccine and a compound of the formulas (I) through (IV) defined herein. The IBDV and the compound represented by formulas (I) through (IV) are administered in amounts effective to produce an immune response to the avian subject. As used herein, an "immunogenic amount" is an amount that is effective to induce an active immune response in the avian subject.

The IBDV vaccine may be of any type known in the art. Exemplary vaccines include, but are not limited to, live, attenuated and killed IBDV vaccines. Alternatively, the vaccine may be a subunit vaccine whereby an IDBV immunogen is expressed and administered to the subject using another virus (or other vaccine vector). As a further alternative, the vaccine may be a naked DNA vaccine. In preferred embodiments of the invention, the IDBV vaccine is a live (including live attenuated) virus vaccine. In more preferred embodiments, the vaccine is a live pathogenic virus vaccine. The compounds of formulas (I) through (IV) may be advantageously co-administered with live pathogenic vaccines to improve the safety thereof (e.g., by reducing pathogenic effects).

For the purpose of the invention, the term "live pathogenic virus" refers to a virus vaccine capable of causing disease or death if not for the co-administration of a compound of formula (I) through (IV) set forth herein. The pathogenicity of the virus may be inherent in the virus itself or due to the susceptibility of the avian subject to be treated (e.g., chickens in ovo). Alternatively, the term "pathogenic", as used to describe virus vaccines herein, typically means that the harm caused subjects by administration of the virus vaccine outweighs any benefit which would result therefrom. In general, more strongly pathogenic viruses (e.g., less attenuated viruses and/or non-attenuated viruses) are preferred. The virus vaccine should be capable of producing an active immune response thereto in the avian subject being treated.

The terms "protective immunity" or "protective immune response," as used herein, are intended to mean that the host bird mounts an active immune response to the virus vaccine, such that upon subsequent exposure to the virus or a virulent viral challenge, the bird is able to combat the infection. Thus, a protective immune response will decrease the incidence of morbidity and mortality from subsequent exposure to the virus among host birds. It is possible that with co-administration of the compound of formulas (I) through (IV) there will be a reduction in the immune response to the virus, but this diminishment will not be so severe that the effectiveness of the vaccine to protect the bird against future virus exposure is substantially or totally eliminated. Those skilled in the art will understand that in a commercial poultry setting, the production of a protective immune response may be assessed by evaluating the effects of vaccination on the flock as a whole, e.g., there may still be morbidity and mortality in individual vaccinated birds.

"Active immune response", as used herein, is intended to mean an immunogenic response of the subject to an antigen. In particular, this term is intended to mean any level of protection from subsequent exposure to virus or virus antigens which is of some benefit in a population of subjects, whether in the form of decreased mortality, decreased lesions, improved feed conversion ratios, or the reduction of any other detrimental effect of the disease, and the like, regardless of whether the protection is partial or complete. An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development cell-mediated reactivity, or both." Herbert B. Herscowitz, *Immunophysiology: Cell Function and Cellular Interactions in Antibody Formation,* in IMMUNOLOGY: BASIC PROCESSES 117 (Joseph A. Bellanti ed., 1985). Alternatively stated, an active immune response is mounted by the host after exposure to immunogens by infection, or as in the present case, by vaccination. Active immunity can be contrasted with passive immunity, which is acquired through the "transfer or preformed substances (antibody, transfer factor, thymic graft, interleukin-2) from an actively immunized host to a non-immune host." Id.

According to preferred embodiments of the present invention, the compound of formulas (I) through (IV) is incorporated in a pharmaceutical formulation and administered in an amount effective to reduce (i.e., ameliorate, delay, diminish, and/or decrease) any pathogenic effects (e.g., disease, mortality, etc.) caused to the avian subject by the administration of the IBDV vaccine, without blocking the production of a protective immune response in the bird. The methods for producing active immunity against IBDV may also comprise administering a pharmaceutical formulation comprising a compound of the formula (I) through (IV) and a pharmaceutically acceptable carrier. By "reduce" it is not necessarily meant that there be no detrimental effects from the virus vaccine. The inclusion of the compound of formulas (I) through (IV) in the pharmaceutical formulations can ameliorate the pathogenic effects of the virus vaccine, such that the benefits of vaccination outweigh the detriments. Alternatively stated, the inclusion of the compound of formulas (I) through (IV) can significantly reduce (i.e., ameliorate, delay, diminish, and/or decrease) the pathogenic effects normally seen after administration of the virus vaccine in the absence of the compound of formulas (I) through (IV).

While not wishing to be held to any particular theory of the invention, it appears that effective doses of the compound of formulas (I) through (IV) protect the bird against the pathogenic effects of the virus, but allow production of an active and protective immune response. According to preferred embodiments of the present invention, the dose of the compound of formulas (I) through (IV) should not be so high that a protective immune response is prevented. Accordingly, according to the present invention of the compound of formulas (I) through (IV) is administered in an amount sufficient to reduce any pathogenic effects of the vaccine, but in an amount insufficient to prevent the development of an active immune response to the vaccine.

With respect to the degree of protection provided by the compound of formulas (I) through (IV), the quantity of the compound of formulas (I) through (IV) administered in combination with the virus vaccine need not be sufficient to provide complete protection from the pathogenic effects of the virus, as long as the detrimental response produced by the virus is reduced to a level at which the benefits of the immune response produced outweigh any harm resulting from the vaccination.

The vaccine may be administered to the avian subject in accordance with the techniques and materials (e.g., pharmaceutically acceptable carriers) described herein.

With respect to all the methods described herein, a therapeutically effective dosage of any specific compound, the use of which is in the scope of present invention, will vary somewhat from compound to compound, avian subject to avian subject, and will depend upon the condition of the avian subject and the route of delivery. A dosage from about 1 mg/kg to about 15 mg/kg of subject body weight, or about 20 mg/kg of subject body weight, or even about 25 mg/kg of subject body weight may be employed for intravenous injection or oral administration.

Pharmaceutical formulations of the present invention may comprise compounds of the present invention in lyophilized form. Alternatively, pharmaceutical formulations of the present invention may comprise compounds of the present invention in a pharmaceutically acceptable carrier. Such pharmaceutical formulations are generally made by admixing the compounds described herein with a pharmaceutically acceptable carrier. Pharmaceutically acceptable carriers are preferably liquid, particularly aqueous, carriers, the selection of which are known in the art. For the purpose of preparing such formulations, the compound may be mixed in a buffered saline (e.g., pH 6 to 8) or conventional culture media. The formulation may be stored in a sterile glass container sealed with a rubber stopper through which liquids may be injected and formulation withdrawn by syringe.

Formulations used in the methods of the present invention may optionally contain one or more adjuvants, the selection of which may be carried out without undue experimentation by the skilled artisan. Preferably, adjuvants such as Freund's adjuvant, aluminum hydroxide, aluminum phosphate, plant and animal oils, and the like can be used. Any suitable stabilizer can be used, including carbohydrates such as sorbitol, mannitol, starch, sucrose, dextran, or glucose; proteins such as albumin or casein; and buffers such as alkaline metal phosphate and the like.

The concentration of the compound of the present invention or a pharmaceutically acceptable salt thereof in a formulation of the present invention may be determined by the skilled artisan and will vary according to certain conditions, including the characteristics of subject being treated (e.g., species, age, weight), the severity and type of the infecting virus or the strain that the subject is being vaccinated against, the dosage form being used, and the like.

The invention will now be described in greater detail with reference to the following examples. It should be noted that these examples are for illustrative purposes only, and are not meant to limit the invention.

Formulas for specific compounds referred to in the examples are set forth below:

Compound DB197

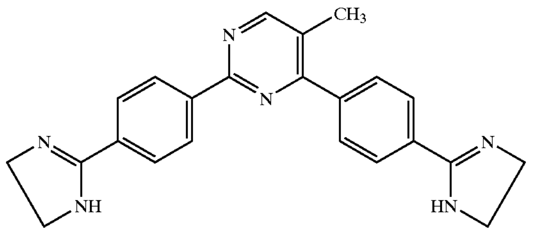

Compound DB203

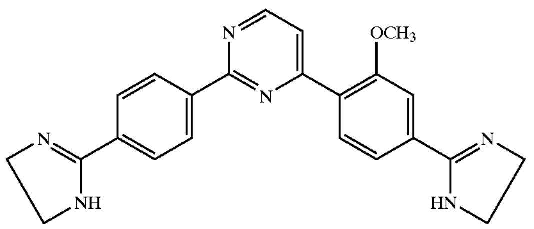

Compound DB453

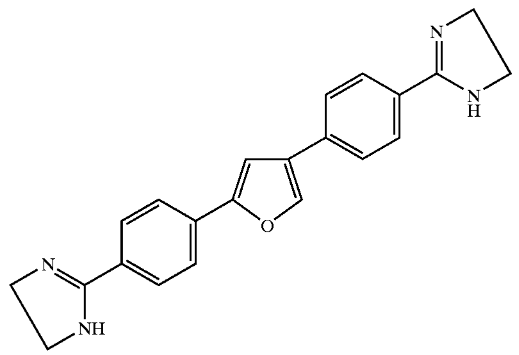

Compound DB092

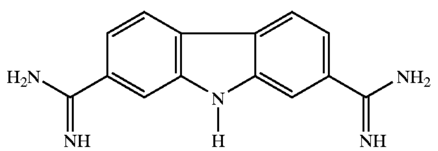

-continued

Compound BABIM

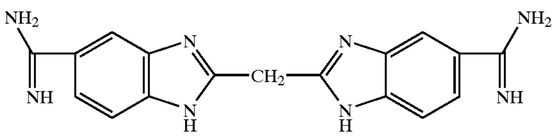

Compound SW066

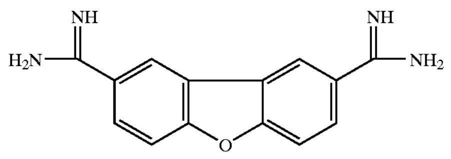

EXAMPLE 1

Synthesis of 2,4-Bis[4,5-dihydro-1H-imidazol-2-yl) phenyl]furan Dihydrochloride A compound of formula (IV) was synthesized as follows. 0.40 g (6.66 mmol) of dried and freshly distilled 1,2-diaminoethane (distilled from KOH) was added to a suspension of 0.80 g (1.84 mmol) imidate ester hydrochloride in 35 ml of dry ethanol (distilled from Mg metal). Under exclusion of water, the solution was refluxed for 22 hours. The resulting suspension was cooled to room temperature. The solid was filtered, washed with ether, and dried in vacuo. The product (0.65 g) was suspended in 50 ml of dry ethanol and the mixture was saturated with HCl gas at ice bath temperature. After stirring overnight, the imidazoline salt was diluted with 20 ml dry diethyl ether (distilled from sodium/benzophenone), filtered, and dried in vacuo at 60° C. for 18 hours to give a pale green solution. Yield: 0.61 g (74%), m.p. >300° C. decomposition. $^{1}$H-NMR (DMSO-$d_6$) δ 8.21 (s, 1 H), 7.90–7.78 (m, 8 H), 7.48 (s, 1 H), 3.96 (t, 8 H), $^{13}$C-NMR (DMSO-$d_6$) δ 167.0, 166.9, 154.7, 143.7, 139.1, 136.6, 130.5, 128.7, 127.9, 125.8, 122.3, 1220.0, 108.6, 46.0, Anal. calculated for $C_{22}H_{20}N_{40}$ HCl $H_2O$ (447.356): C, 59.06; H, 5.41; N, 12.52. Found: C, 59.39; H, 5.25; N, 12.44.

EXAMPLE 2

In Vitro Evaluation of Effect of Compounds on IBDV Replication

Cell and virus propagation: Chick embryo fibroblasts (CEF) were obtained from 10 to 12 day old specific pathogen free (SPF) eggs from SPAFAS, Inc. of Preston, Conn. Secondary cultures of CEF were passaged in DMEM with one percent tryptose phosphate broth, 10 percent heat inactivated fetal bovine serum and antibiotics. Delaware Variant A strain of IBDV was propagated in secondary cultures of chick embryo fibroblast cells (see Luckert, P. D., et al., *Avian Dis.* 18, 243–251 (1974)). Tissue culture infective dose (TCID) and the Embryo Infective Dose (EID) was determined using the known method of Reed and Muench. See L. J. Reed and H. Muench, *Am. J. Compar. Pathol.* 85, 597–610 (1937). The same virus lot was used throughout the studies described herein ($TCID_{50}$=102). All virus inoculums were tested by PCR assay at the Alabama State Diagnostic Labaratory for possible chick infectious anemia virus contamination.

In vitro assay: A system was developed to sustain viral replication and evaluate the ability of a compound of the invention to inhibit viral replication, as follows: cells were harvested from culture flasks and 100 μl placed in 96 well plates for the assay ($5\times10^4$ cells/well). Cells were incubated overnight to allow adherence. The media was removed and a dilution of Variant A virus stock was added to each well (5 replicates each time per point). Virus was incubated with cells for 1 hour at 38° C. Unattached virus was washed away and the cells were incubated in Dulbecco's Modified Eagle's Medium (DMEM) with one percent tryptose phosphate broth, five percent heat inactivated fetal bovine serium, and antibiotics. Various concentrations of compounds of formulas (I) through (IV) are used to treat cells exposed to IBDV. The compounds are maintained in the culture media throughout the experiments. At the time points indicated, the cells were frozen and thawed three times to release virions.

Determination of level of viral replication. The level of Delaware Variant A strain replication was determined using the viral antigen capture ELISA. Briefly, polyclonal avian anti-IBDV antisera (SPAFAS, Inc. of Preston, Conn.) was diluted 1000-fold in carbonate-bicarbonate buffer (Sigma #C-3641, Sigma Corporation, St. Louis, Mo., USA), pH 9.5, and adsorbed to 96-well plates overnight at room temperature (100 μl/well). Plates were then washed in phosphate-buffered saline (PBS) containing 0.1 percent of TWEEN™ 20. Test samples were incubated in triplicate for two hours. After washing twice with N/PBS/TWEEN to remove unadsorbed virus, a monoclonal anti-IBDV antibody (R63) was allowed to bind (ATCC number: HB-9490), also for a two hour incubation at room temperature. The monoclonal antibody was harvested from hybridoma clone culture supernatant and diluted 1:50 in dilution buffer (KPL, Inc., Gaithersburg, Md., USA). The monoclonal antibody is believed to recognize an epitope on VP2. The detection step included a horseradish peroxidase antibody conjugate (KPL, Inc.). The plates were read after 1 hour incubation with the enzyme substrate ABTS at 405 nm. Triplicate values from the microplate reader were averaged and calculated as a percent of control. Test samples were compared to control values by t-test ($\alpha$=0.05).

EXAMPLE 3

Results of In Vitro Screening

The ability of various compounds to inhibit IBDV replication was evaluated using the assay set forth in Example 2. The compounds evaluated included DB181, KAO111, AP087, DAP032, RAO113, SW066, DAP092, DAP021 and BABIM. The compounds were maintained in the culture medium throughout the experiment. Dicationic molecules with imidazoline side groups were included as negative controls. It is believed that these dicationic molecules lack serine protease inhibitory activity although similar to dicationic amidines in structure. See Tidwell, R. R. et al., *J. Med. Chem.* 21, 613–623 (1978). The compounds DB181, KAO111, AP087, are imidazolines and did not significantly inhibit virus replication. The other compounds tested showed some effect at higher concentrations. The most significant decrease of virion formation was observed with compounds BABIM, SW066, and DAP092.

FIG. 1 illustrates single step growth curves of IBDV in chick embryo fibroblasts treated with varying concentrations of BABIM, SW066, and DAP092. In FIG. 1, the x-axis values represent drug concentration in micromolar (μM); the y-axis values represent levels of viral replication as expressed in percentage of control (i.e., percentage of level of viral replication in infected cells not treated with drug or treated with a compound that is known not to effect viral replication). Data points represented by triangles are data obtained from treatment of infected cells with the drug DAP092; data points represented by circles are data obtained from treatment of infected cells with the drug SW066; the remaining line represents data obtained from treatment of infected cells with the drug BABIM.

EXAMPLE 4

Toxicity of BABIM, SW066, and DAP092

BABIM, SW066, and DAP092 were assessed for cell toxicity using the MTT assay for cell viability described in T. Mossman, *J. Immunol. Methods* 65, 55–63 (1983). Briefly, cells were grown in cell culture according to Mossman, using media that did not contain phenol red. 10 μl of MTT reagent was added to each wall and incubated for four hours at 38° C. Acid-isopropanol was added to stop the reaction and plates were read within one hour at 570 nm and 630 nm. The 630 nm reading was subtracted from the 570 nm reading. No toxicity was reported for BABIM. The MTT assay indicated that some toxicity may be associated with SW066 and DAP092 at the highest concentration tested, 1 mM.

EXAMPLE 5

Quantitation of Effect of Compounds on IBDV Inhibition

The CEF assay generally described above in Example 2 was performed to quantitate the level of virus inhibition exhibited by BABIM, SW0A66, and DAP092. Log dilutions of IBDV Variant A were used to infect cells in the presence of 0.1 mM of each drug, or in the absence of any drug.

Figure 2:
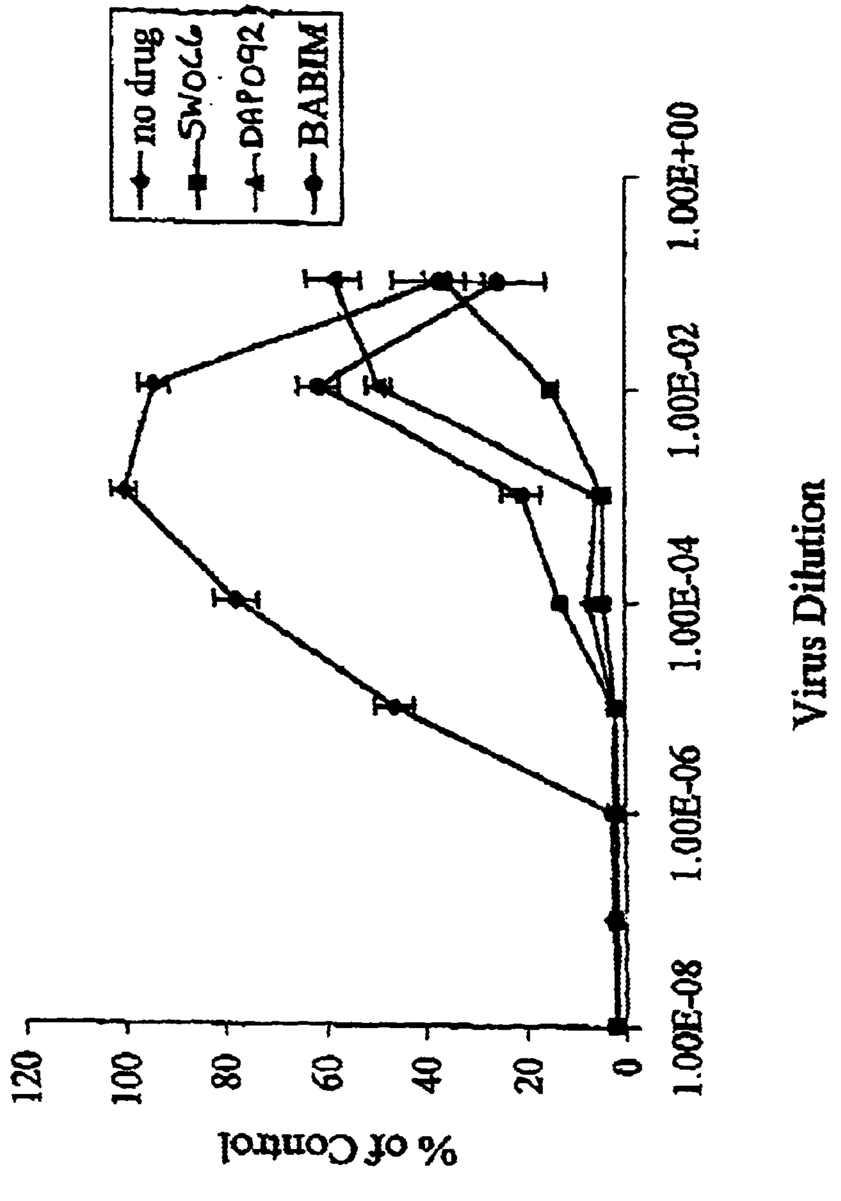
FIG. 2 is a graphical illustration of the effect of the drugs BABIM, SW066, and DAP092 at a concentration of 0.1 millimolar (mM) on IBDV Variant A inhibition.

The results of this study are illustrated in FIG. 2. In FIG. 2, the x-axis values represent the log dilution of IBDV Variant A; the y-axis values represent the level of virus inhibition as expressed in percentage of control. The uppermost line represents data obtained from untreated infected cells (the "no drug" control). Of the additional lines, the data points represented by triangles are data obtained from treatment of infected cells with the drug DAP092; data points represented by squares are data obtained from treatment of infected cells with the drug SW066; and data points represented by circles are data obtained from treatment of infected cells with the drug BABIM.

The level of virus inhibition was found to be greater than two logs of virus for the three compounds tested. In this study, SW066 was the most effective in decreasing virion formation. The cell cultures were also examined with an inverted microscope for cytopathic effect (CPE). At the highest concentration of virus in the "no compound" control, there was significant cell loss due to virus activity. Very little CPE was observed in the SW066 and DAP092-treated samples at the same dilution of virus. These two compounds appear to have a significant effect in reducing IBDV production, even at the high concentrations of virus.

EXAMPLE 6

Drug Addition and Removal Studies

Figure 3A:
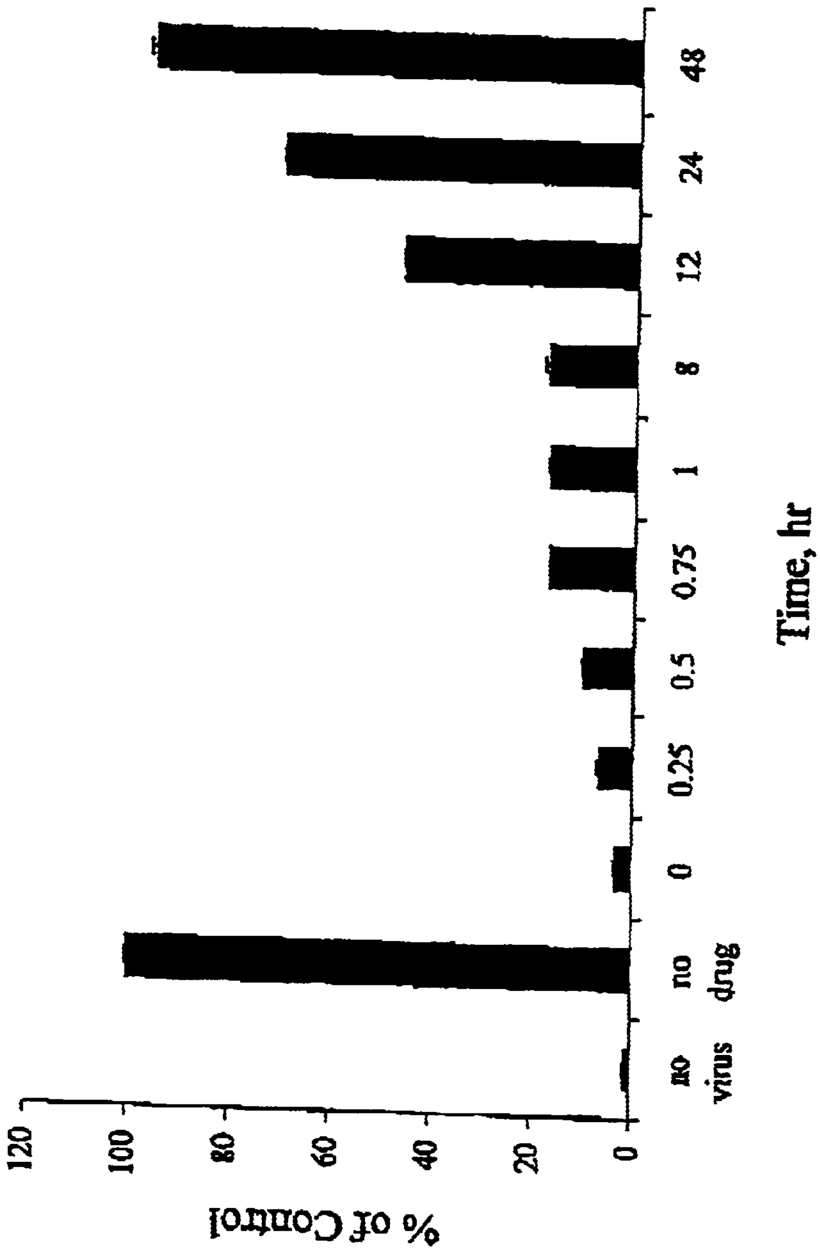
FIGS. 3A and 3B are graphical illustrations of the effect of treating cells with the drug SW066 at various time points after IBDV infection, thus illustrating which stages of the virus life-cycle are affected by the drug.
Figure 3B:
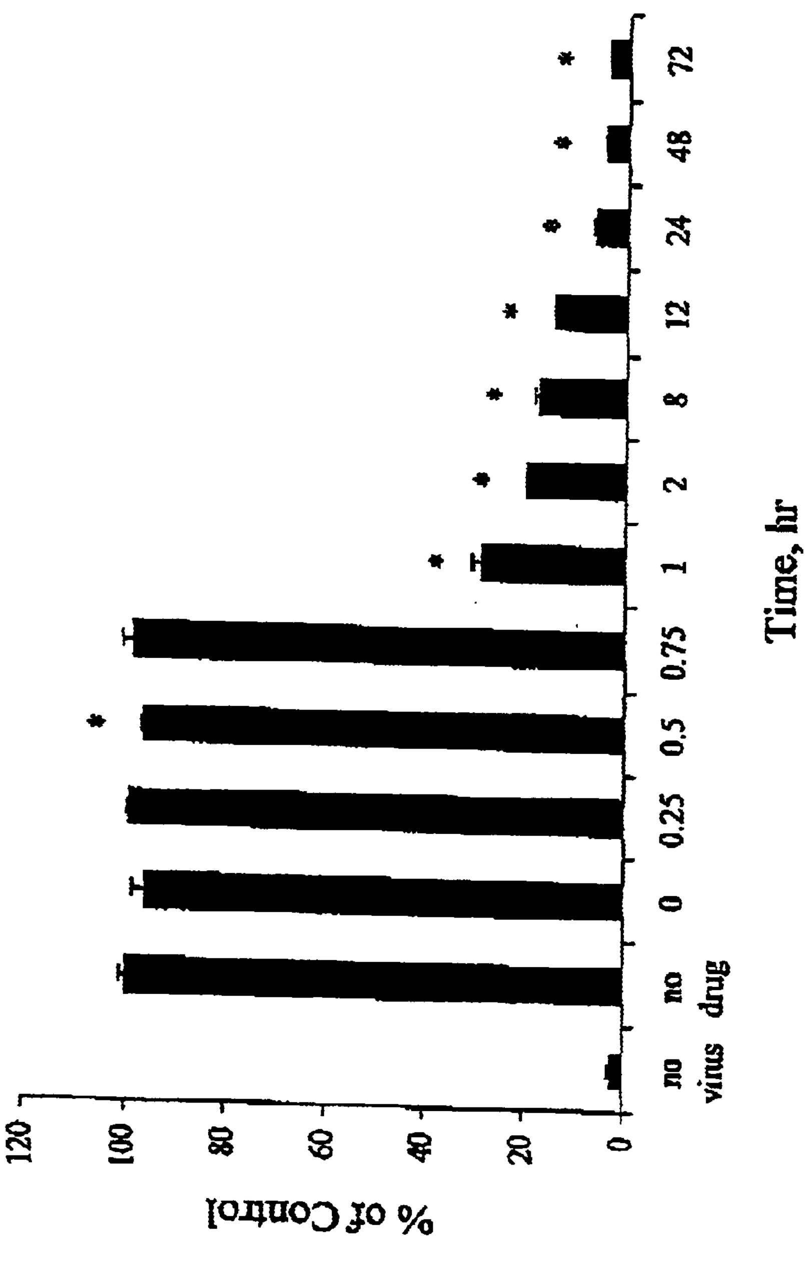

Cells were treated with SW066 at various time points after infection to evaluate the virus life-cycle stage affected by the compound (see FIGS. 3A and 3B). In FIGS. 3A and 3B, the x-axis values represent time elapsed in hours; the y-axis values represent the level of viral replication (or inhibition thereof) as expressed in percentage of control.

FIG. 3A shows there is a potentially substantial inhibition of virus replication when SW066 is added prior to the 12 hour incubation time point. When SW066 is added after 12 hours, very little potential effect on virus production is observed. FIG. 3B illustrates a similar experiment wherein SW066 was introduced at the beginning of the incubation and then removed by washing and replaced with fresh media at the time points shown in FIG. 3B. The compound removed prior to one hour is believed to have little or no affect on virion formation. A significant decrease in virus production was observed when SW066 remains in the culture past the one hour time point.

EXAMPLE 7

Effect of Trypsin on the IBDV Life Cycle

It is known that the addition of trypsin can enhance the attachment and penetration of respiratory syncytial virus and rotavirus. A trypsin competition experiment was performed in order to confirm that the activity of the inventive compounds of the present invention is not the result of protease-mediated virus attachment or penetration, as follows: trypsin (1 mg/ml) was added to the cells in culture described above in Example 6. Trypsin will compete with SW066 at the cell surface, but the presence of trypsin was not found to inhibit the drug's activity.

EXAMPLE 8

Virucidal Effect of the Compounds of the Invention

IBDV-infected cells were treated with varying concentrations (0.01 μM, 0.1 μM, 1 μM, 10 μM and 100 μM) of SW066 for 24 hours. After 24 hours, SW066 was washed away from the cell. After 72 hours of total incubation time (i.e., after the life cycle of IBDV is predicted to be complete), the resulting virions were harvested, as described above.

In order to determine if the virions produced in the presence of drug are viable, varying dilutions of these viral preparations were used to inoculate a second set of CEF cultures. Concentrations of the viral dilutions were as follows: 1.00E-10, 1.00E-09, 1.00E-08, 1.00E-07, 1.00E-06 and 1.00E-05. After 72 hours of incubation, cells were treated by a freeze-thaw method to harvest viral particles, and were assayed by ELISA as described in Example 2. The results of this experiment indicated that the virucidal effect of SW066 is not transient. The second set of cultures, with the exception of the $10^{-5}$ dilution of virus, did not propagate virus when the first set of cultures were treated with the drug at 100 μM. The long term drug effect was also observed for some virus dilutions at 10 μM of drug. The lowest concentration of drug that demonstrated anti-viral activity in this experiment was 1 μM with the $10^{-10}$ dilution of virus.

EXAMPLE 9

Chicken Embryo Challenge Study

Ten day old chick embryos were inoculated with IBDV, APHIS strain, by the chorio-allantoic membrane route ($EID_{50}=10^{7.8}$/ml). Five replicates were inoculated for eight log dilutions of virus. An $EID_{50}$ was determined. See Reed and Muench, supra. The eggs were candled for 8 to 10 days to check viability. Surviving embryos were necropsied and examined for gross legions. Body and organ weights were determined for thymus, spleen, and bursa. These organs were fixed in paraformaldehyde and examined for histopathology. Various concentrations of virus and compounds are used to treat eggs. Flow cytometry was performed on the spleen cells, e.g., CD4, CD8, Ia and sig (B-cell) cells.

The embryos were treated with Hank's balanced salt solution (HBSS), SW066, or DAP092. Treatment with SW066 and DAP092 did not alter the $EID_{50}$. However, embryo death was delayed for approximately 24 hours. Surviving chicks appeared normal in organ weights, histopathology, and flow cytometry. This result indicates that the compounds can affect the replication of IBDV in vivo.

EXAMPLE 10

In Vivo Drug Treatment Protocol and Results

SPF leghorn chickens were challenged at three weeks of age with an 100 EID APHIS isolate of IBDV. Approximately 12 birds were contained in an isolator unit with four units being employed. In each isolator unit, two birds received either drug or a placebo. One unit contained uninfected controls. The birds are treated with the drugs SW066, DAP092, DB453, DB197, and DB203 for three days. Half of the drug dosage was administered in the nares, while the second half was administered in the cloaca, at a dosage of 20 mg/kg. At necropsy, the birds were weighed, their bursa removed, weighed, and ground with a tissue homogenizer. The ground bursa material was evaluated for lymphocyte counts and viral load.

In general, the placebo controls were found to have heavily infected, edematous bursas upon necropsy. Those treated with DB197 or DB203 appeared identical to those from the uninfected control group. Immunologically, treatment with DB197 or DB203 resulted in the maintenance of relatively normal lymphocyte populations three days after infection. The results are presented below in Table 1.

TABLE 1

Results of *in vivo* drug treatment: Lymphocyte Population Per Gram of Bursal tissue.

| Treatment | Percentage Uninfected Control | P value |
|---|---|---|
| Placebo | 3.57 | |
| SW066 | 4.3 | |
| DB197 | 60.5 | .00154 |
| DB258 | 22.3 | |
| DB203 | 51.3 | |
| DAP092 | 10.3 | |

The data indicates that the drug treatment leaves the bursa tissue clinically normal, preventing the immunosuppression that often occurs with IBDV infection. The virus counts generally remained high for all groups, with little or no differences seen from the control. It is possible that the sensitivity of the test indicated that the inoculum was still possibly present in the bursa.

EXAMPLE 11

Evaluation of Drug Effect to Prevent or Inhibit IBD

Chicks were placed in four groups of nine birds each. The four groups were: (1) no virus control (placebo), (2) no virus control (treated with SW066), (3) APHIS IBDV strain at 130 EID (placebo), and (4) APHIS IBDV strain at 130 EID (treated with SW066). The birds were challenged at two weeks of age with 10 μL of the APHIS strain divided between the eye and nares. The drug was administered orally, one mL at a concentration of five mg/mL. Previous studies have indicated that a dosage of 20 mg/kg of body weight is advantageous; in this case, the solubility of the drug and the volume of oral intake dictated the initial dose for this experiment. Daily drug treatment began the same day and 30 minutes prior to challenge. After seven days, survivors were sacrificed and necropsied. Two birds died in each challenge group.

The virus is believed to cause necrosis in the bursa and to reach a plateau of virus level at three days post-challenge. As the inflammation begins to subside, the organ decreases in size and is severely atrophied at seven to ten days post-challenge. The bursa weight is accordingly a measure of bursal disease severity and was used in this experiment to detect differences between treatment groups. The bursa weights were higher in the drug treatment group compared to the placebo group and significantly different at p=0.05. These results indicate a more severe depletion of the bursa in the placebo group as compared to the drug group.

Post-challenge titers for the infected groups were not significantly different. Bursa histology results of infected birds were significantly different for the placebo and drug groups. While all birds in the placebo group (n=6) received a scoring of four, i.e., all follicles are depleted of lymphocytes with loss of follicular structure, two birds in the drug group (n=7) were scored as three, i.e., the majority of follicles are severely depleted of lymphocytes. The remaining birds were scored as four. These data indicate the drug SW066 provides some protection from IBDV induced B-cell depletion.

EXAMPLE 12

Evaluation of Drug Effect to Prevent or Inhibit IBD

The procedure according to Example 11 was carried out, with a variation in which chicks were placed in six groups of ten birds each, as follows: (1) no virus control (oral placebo), (2) no virus control (SW066 intravenous), (3) no virus control (prodrug of SW066 oral), (4) APHIS IBDV strain 130 EID (oral placebo), (5) APHIS IBDV strain 130 EID (SW066 intravenous), and (6) APHIS IBDV strain 130 EID (prodrug of SW066 oral). The birds were challenged at three weeks of age with 100 μl of APHIS strain divided between the eye and nares. Drug was administered intravenously or orally. The prodrug version of SW066 was used via the oral route to enhance absorption. Daily drug treatment began the same day and thirty minutes prior to challenge. After seven days, survivors were sacrificed and necropsied.

No statistical significant difference in the bursa weight of survivors was observed. However, mortality was different for the treatment groups. The intravenous drug group may indicate substantial protection from the virus at 10% mortality compared to 40% and 30% mortality in the placebo and prodrug treatment groups, respectively. Although not wishing to be bound by any theory, this result may be due to the low numbers of birds used. Post-challenge antibody titers were significantly different between both drug treatment groups and the placebo group. The prodrug and intravenous groups were not significantly different for antibody titers.

EXAMPLE 13

Leghorn Drug Study

The procedure according to Example 12 was carried out with the following modifications: the drugs SW066, DB197, DB528, DB203 and DAP092 were tested in three week old Leghorns for protection against 100 EID of APHIS strain IBDV. The drugs were suspended in histidine-saline and used at a concentration of 4 mg/ml. One mL of drug was administered orally on the day of challenge (30 minutes prior to challenge), 24 hours PI and 48 hours PI. Birds were euthanised by $CO_2$ inhalation and necropsied at three days post-challenge. Each drug and placebo cohort consisted of eight leghorns. Birds were weighed and sorted on the day of challenge to co-mingle birds of different weights and monitor drug dose per body weight. Birds were raised in isolation units. Each unit held 12 birds, two birds for each of the six cohorts (i.e., placebo, SW066, DB197, DB528, DB203 and DAP092). In addition, 12 uninfected birds were housed in a separate isolation unit.

Figure 4:
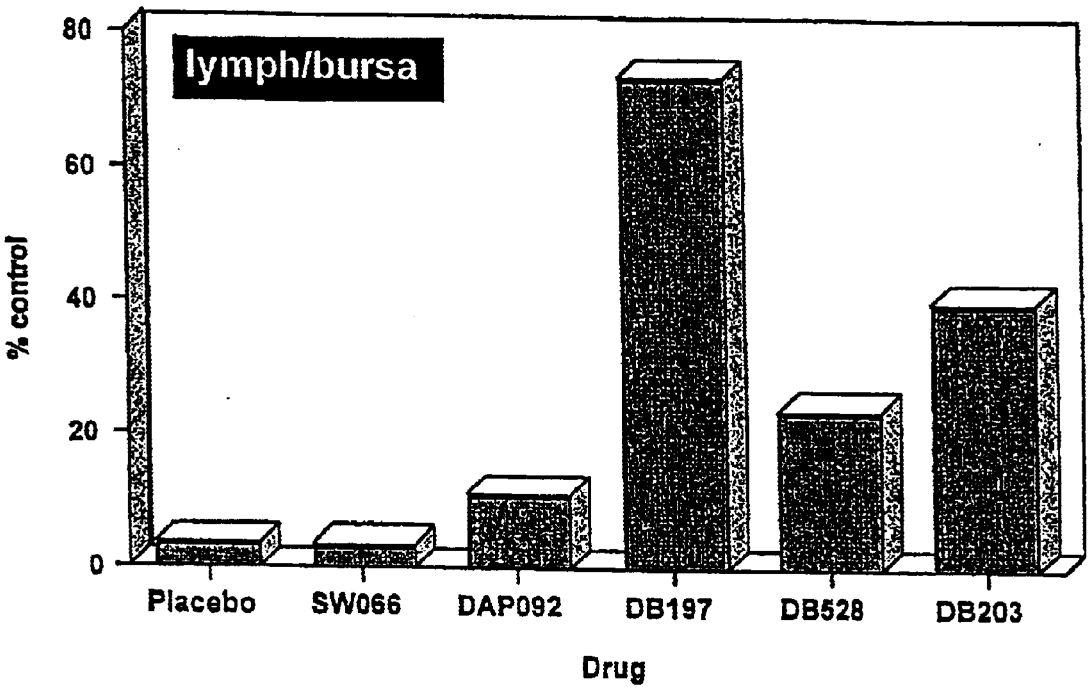
FIG. 4 is a graphical illustration of the ability of certain compounds of the present invention to prevent or inhibit IBDV.

The viral load of the bursa was determined by antigen capture ELISA, as described in Example 2, while absolute lymphocyte cell counts were determined by hemocytometer. DB197 demonstrated the most protection with DB203, DB528, DAP092, and SW066 exhibiting decreasing protection in the following consecutive order (DB197>DB203>DB528>DAP092>SW066). The lymph per bursa cell number was the highest in this group, but still significantly different from uninfected controls (t-test, p-value=0.01). The results of this experiment are set forth in FIG. 4.

In the specification, and examples there have been disclosed typical preferred embodiments of the invention and, although specific terms are employed, they are used in a generic and descriptive sense only and not for the purposes of limitation, the scope of the invention being set forth in the following claims.

That which is claimed:

1. A method of treating infectious bursal disease (IBD) in an avian subject in need of such treatment, said method comprising administering to said subject a compound selected from the group consisting of:

(I)

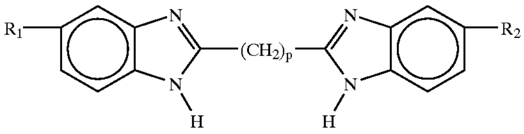

(II)

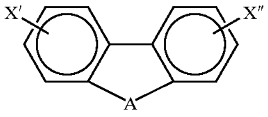

(III)

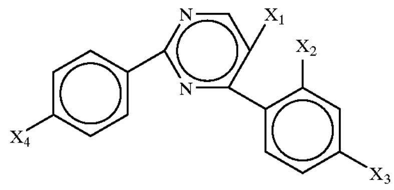

and (IV)

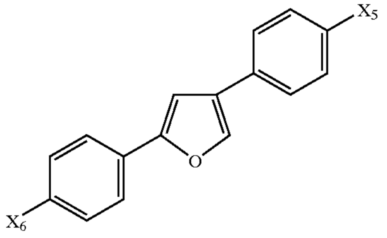

or the pharmaceutically acceptable salts thereof, wherein:

p is an integer ranging from 1 to 8;

A is selected from O, S, and NR wherein R may be H or loweralkyl;

X', X", $X_3$, $X_4$, $X_5$, $X_6$, $R_1$, and $R_2$ are independently selected and each represented by loweralkyl, loweralkoxy, alkoxyalkyl, hydroxyalkyl, aminoalkyl, alkylaminoalkyl, cycloalkyl, aryl, alkylaryl, halogen, or:

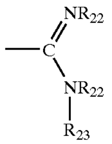

wherein Each $R_{22}$ and $R_{23}$ is independently selected from the group consisting of H, loweralkyl, alkoxyalkyl, hydroxyalkyl, aminoalkyl, alkylaminoalkyl, cycloalkyl, aryl, and alkylaryl, or two $R_{22}$ groups together represent $C_2$–$C_{10}$ alkyl hydroxyalkyl, or alkylene; or the two $R_{22}$ groups together represent cycloalkyl or;

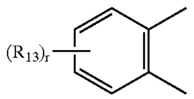

wherein r is from 1 to 3 and $R_{13}$ is H,

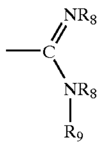

or —$CONHR_{10}NR_{11}R_{12}$, wherein:

$R_{10}$ is loweralkyl; $R_{11}$ and $R_{12}$ are independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, and alkylaryl, or two $R_8$ groups together represent $C_2$–$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl; wherein X' and X" may be in the meta or para positions;

$X_1$ and $X_2$ are independently selected from H, loweralkyl, or loweralkoxy;

and wherein said compound thereof is administered in an amount sufficient to treat IBD.

2. The method according to claim 1, wherein the avian subject is a chicken.

3. The method according to claim 1, wherein said compound is represented by the formula:

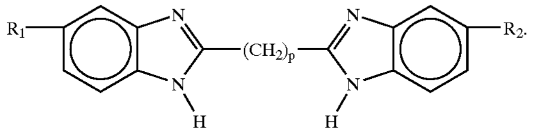

4. The method according to claim 1, wherein said compound is represented by the formula:

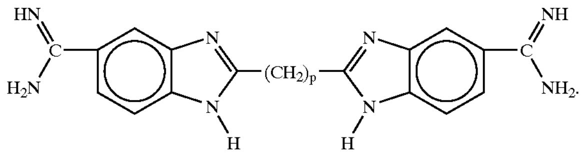

5. The method according to claim 1, wherein said compound is represented by the formula:

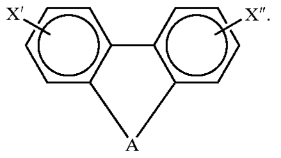

6. The method according to claim 5, wherein said compound is represented by the formula:

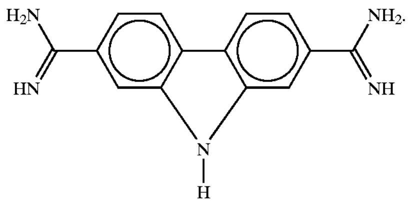

7. The method according to claim 5, wherein said compound is represented by the formula:

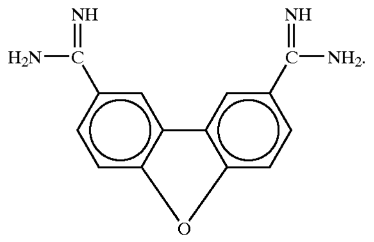

8. The method according to claim 1, wherein said compound is represented by the formula:

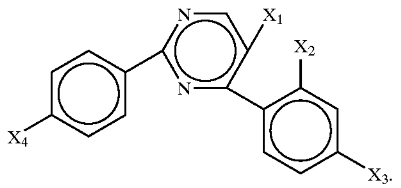

9. The method according to claim 8, wherein said compound is represented by the formula:

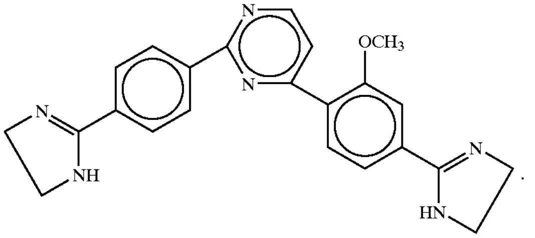

10. The method according to claim 1, wherein said compound is represented by the formula:

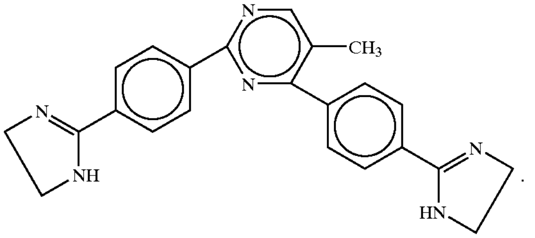

11. The method according to claim 1, wherein said compound is represented by the formula:

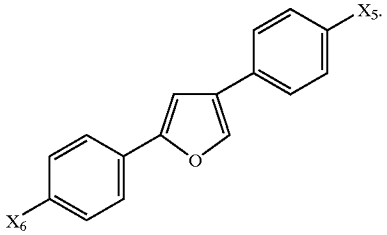

12. The method according to claim 1, wherein said compound is represented by the formula:

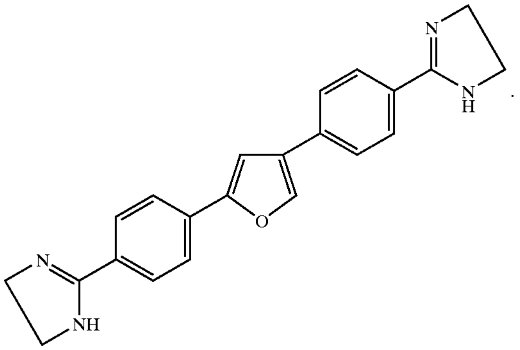

13. The method according to claim 1, wherein said compound is present in a pharmaceutical formulation, and wherein said pharmaceutical formulation further comprises a pharmaceutically acceptable carrier.

14. The method according to claim 13, wherein said compound is represented by the formula:

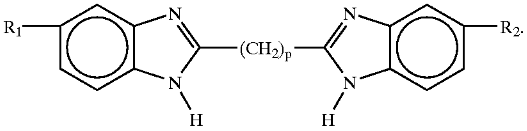

15. The method according to claim 14, wherein said compound is represented by the formula:

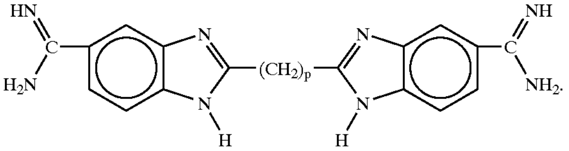

16. The method according to claim 13, wherein said compound is represented by the formula:

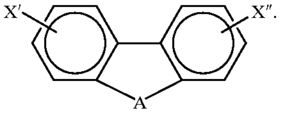

17. The method according to claim 16, wherein said compound is represented by the formula:

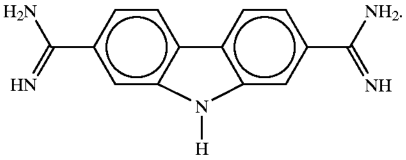

18. The method according to claim 16, wherein said compound is represented by the formula:

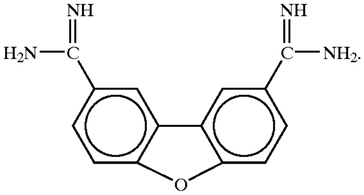

19. The method according to claim 13, wherein said compound is represented by the formula:

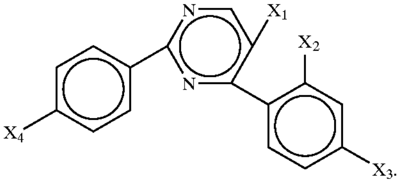

20. The method according to claim 19, wherein said compound is represented by the formula:

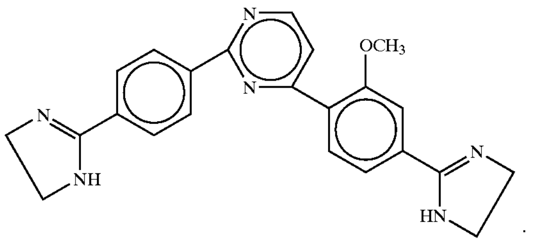

21. The method according to claim 19, wherein said compound is represented by the formula:

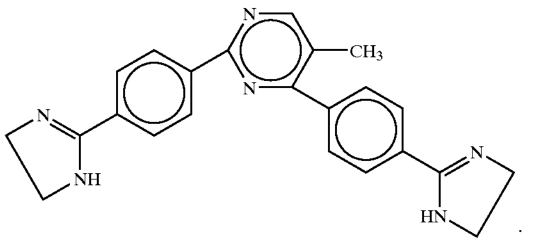

22. The method according to claim 13, wherein said compound is represented by the formula:

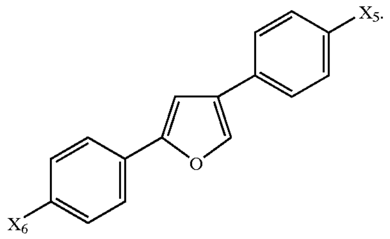

23. The method according to claim 22, wherein said compound is represented by the formula:

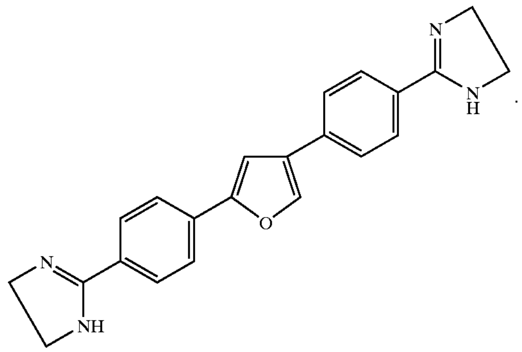

24. The method according to claim 13, wherein said administering step is administered to said avian subject in ovo.

25. The method according to claim 13, wherein said administering step is administered to said avian subject post-hatch.

* * * * *